US012209068B2

(12) United States Patent
Goodarznia et al.

(10) Patent No.: US 12,209,068 B2
(45) Date of Patent: Jan. 28, 2025

(54) INTEGRATION OF OXIDATIVE DEHYDROGENATION PROCESS WITH CATALYTIC MEMBRANE DEHYDROGENATION REACTOR PROCESS

(71) Applicant: NOVA CHEMICALS (INTERNATIONAL) S.A., Fribourg (CH)

(72) Inventors: Shahin Goodarznia, Calgary (CA); Vasily Simanzhenkov, Calgary (CA); Bolaji Olayiwola, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 85 days.

(21) Appl. No.: 18/030,199

(22) PCT Filed: Oct. 28, 2021

(86) PCT No.: PCT/IB2021/059983
§ 371 (c)(1),
(2) Date: Apr. 4, 2023

(87) PCT Pub. No.: WO2022/096994
PCT Pub. Date: May 12, 2022

(65) Prior Publication Data
US 2023/0357108 A1    Nov. 9, 2023

Related U.S. Application Data

(60) Provisional application No. 63/109,372, filed on Nov. 4, 2020.

(51) Int. Cl.
*C07C 5/48*    (2006.01)
*B01J 19/00*   (2006.01)
(Continued)

(52) U.S. Cl.
CPC .............. *C07C 5/48* (2013.01); *B01J 19/0013* (2013.01); *B01J 19/245* (2013.01);
(Continued)

(58) Field of Classification Search
CPC ......... C07C 5/48; C07C 7/04; C07C 2529/74; C07C 2523/42; C07C 2523/60;
(Continued)

(56) References Cited

U.S. PATENT DOCUMENTS 3,420,911 A    1/1969   Woskow et al.
3,420,912 A    1/1969   Woskow et al.
(Continued)

FOREIGN PATENT DOCUMENTS

WO    WO 2005/115949    12/2005
WO    WO 2013/135390     9/2013
WO    WO 2018/198015    11/2018

OTHER PUBLICATIONS

Dr. Ralf Kriegel, "Energy demand of oxygen membrane plants," Fraunhofer IKTS Annual Report, 2013/14, pp. 76-77.
(Continued)

*Primary Examiner* — Ali Z Fadhel
(74) *Attorney, Agent, or Firm* — Fish & Richardson P.C.

(57) ABSTRACT

This disclosure relates to a process of converting one or more alkanes to one or more alkenes that includes providing a first stream containing one or more alkanes and oxygen to an oxidative dehydrogenation process which converts at least a portion of the one or more alkanes to one or more alkenes in an oxidative dehydrogenation reactor, a second stream exiting the oxidative dehydrogenation process comprising one or more alkanes, and one or more alkenes; and providing at least a portion of the alkanes in the second stream to a catalytic membrane dehydrogenation process containing a catalyst loaded into a catalytic dehydrogenation
(Continued)

membrane reactor which converts at least a portion of the alkanes to the corresponding alkenes and hydrogen.

27 Claims, 4 Drawing Sheets

(51) Int. Cl.
*B01J 19/24* (2006.01)
*B01J 29/89* (2006.01)
*C07C 7/04* (2006.01)

(52) U.S. Cl.
CPC ........... *B01J 19/2475* (2013.01); *B01J 29/89* (2013.01); *C07C 7/04* (2013.01); *B01J 2219/00076* (2013.01); *C07C 2529/74* (2013.01)

(58) Field of Classification Search
CPC ... C07C 5/3337; B01J 19/0013; B01J 19/245; B01J 19/2475; B01J 29/89; B01J 2219/00076; Y02P 20/52
See application file for complete search history.

(56) References Cited

U.S. PATENT DOCUMENTS

| | | | |
|---|---|---|---|
| 4,536,196 A | 8/1985 | Harris | |
| 4,791,079 A * | 12/1988 | Hazbun | B01J 35/59 502/340 |
| 5,276,237 A * | 1/1994 | Mieville | C07C 2/84 585/500 |
| 5,306,411 A * | 4/1994 | Mazanec | C01C 3/0216 204/266 |
| 6,287,432 B1 * | 9/2001 | Mazanec | H01M 8/1231 204/266 |
| 6,355,093 B1 * | 3/2002 | Schwartz | C01C 3/0216 502/4 |
| 7,329,791 B2 * | 2/2008 | Balachandran | C07C 5/3337 585/818 |
| 8,900,523 B2 | 12/2014 | Balachandran | |
| 2002/0173422 A1 * | 11/2002 | Bitterlich | B01J 23/002 502/302 |
| 2007/0151857 A1 * | 7/2007 | Farrusseng | B01D 67/0069 502/4 |
| 2007/0249884 A1 * | 10/2007 | Carrera | C07C 2/08 585/315 |
| 2007/0260101 A1 * | 11/2007 | Carrera | B01J 19/2475 585/654 |
| 2009/0318743 A1 * | 12/2009 | Arnold | C01B 13/0251 585/658 |
| 2012/0310027 A1 * | 12/2012 | Kjolseth | C07C 5/333 427/372.2 |
| 2013/0072737 A1 * | 3/2013 | Kustov | B01J 23/28 585/658 |
| 2014/0018594 A1 * | 1/2014 | Palo | C07C 5/321 422/187 |
| 2014/0249339 A1 * | 9/2014 | Simanzhenkov | B01J 19/245 422/162 |
| 2014/0275679 A1 * | 9/2014 | Sofranko | B01J 23/002 422/186 |
| 2019/0248717 A1 * | 8/2019 | Gaffney | B01J 19/2415 |
| 2021/0291150 A1 * | 9/2021 | Karakaya | C01B 3/501 |
| 2022/0234973 A1 * | 7/2022 | Meiswinkel | C07C 45/50 |
| 2023/0241586 A1 * | 8/2023 | Notestein | B01J 35/23 585/660 |

OTHER PUBLICATIONS

Dr.-Ing. Gerhard Beysel, "Enhanced Cyrogenic Air Separation a Proven Process applied to Oxyfuel Future Prospects," in Linde, 1st Oxyfuel Combustion Conference, Cottbus, Germany, Sep. 8, 2009, slide 20.

Lowe et al., "Hydrogen Membrane Selection for a Water Gas Shift Reactor—Phase II," Third Conference on Carbon Sequestration, Alexandria, VA, May 3-6, 2004, 9 pages.

* cited by examiner

INTEGRATION OF OXIDATIVE DEHYDROGENATION PROCESS WITH CATALYTIC MEMBRANE DEHYDROGENATION REACTOR PROCESS

CROSS-REFERENCE TO RELATED APPLICATIONS

This application is a National Stage Application under 35 U.S.C. § 371 and claims the benefit of International Application No. PCT/IB2021/059983, filed Oct. 28, 2021, which claims priority to U.S. Provisional Application No. 63/109,372 filed on Nov. 4, 2020, the entire contents of which are hereby incorporated by reference.

TECHNICAL FIELD

The present specification is directed to an integrated process for production of olefins and hydrogen. In particular, the process involves an oxidative dehydrogenation process of one or more C2-C4 alkanes to one or more C2-C4 alkenes, and a catalytic membrane dehydrogenation reactor process which can separate the hydrogen generated by the oxidative dehydrogenation process in a catalytic membrane dehydrogenation reactor from the remainder of the product stream.

BACKGROUND ART

Catalytic oxidative dehydrogenation (ODH) of alkanes into corresponding alkenes is an alternative to steam cracking; steam cracking is the method of choice for the majority of today's commercial-scale producers. Despite its widespread use, steam cracking has its downsides. Steam cracking is energy intensive, requiring temperatures in the range of 700° C. to 1000° C. to satisfy the highly endothermic nature of the cracking reactions. This also results in significant amounts of greenhouse gasses. The process is expensive owing to the high fuel demand, the requirement for reactor materials that can withstand the high temperatures, and the necessity for separation of unwanted by-products using downstream separation units. The production of coke by-product requires periodic shutdown for cleaning and maintenance. For ethylene producers, the selectivity for ethylene is only around 80-85% for a conversion rate that does not generally exceed 60%. In contrast, ODH operates at lower temperatures, produces insignificant amounts of greenhouse gasses, does not produce coke, and using newer-developed catalysts provides selectivity for ethylene of around 98% at close to 60% conversion.

The concept of ODH has been known since at least the late 1960s. Since that time, considerable effort has been expended on improving the process, including improving catalyst efficiency and selectivity. In order for ODH to become a mainstream commercial option, the economic benefit must outweigh the risk associated with potential thermal runway of the reaction. Some disclosures are directed at improving the safety and efficiency of the reaction by developing better catalysts and systems for reducing risk.

SUMMARY OF INVENTION

The present disclosure provides an integrated process that includes an oxidative dehydrogenation (ODH) process which converts one or more C2-C4 alkanes to one or more C2-C4 alkenes and a catalytic membrane dehydrogenation reactor (CMDR) process which can separate the hydrogen generated in the CMDR from the remainder of the product stream.

Further, the present disclosure provides a process for the production of one or more C2-C4 alkenes including: i) contacting in an oxidative dehydrogenation process a feed including at least one C2-C4 alkane and oxygen with at least one mixed metal oxide catalyst to produce a product stream which includes unreacted C2-C4 alkane and one or more corresponding C2-C4 alkenes; and ii) passing the product stream to a catalytic membrane dehydrogenation reactor process including at least one membrane containing one or more group 4 elements or group 5 elements to dehydrogenate at least a portion of the unreacted C2-C4 alkane to produce at least one permeate stream that includes hydrogen and at least one retentate stream which includes one or more corresponding C2-C4 alkenes that is substantially free of hydrogen.

BRIEF DESCRIPTION OF THE DRAWINGS

To easily identify the discussion of any particular element or act, the most significant digit or digits in a reference number refer to the figure number in which that element is first introduced.

DESCRIPTION OF EMBODIMENTS

Figure 1:
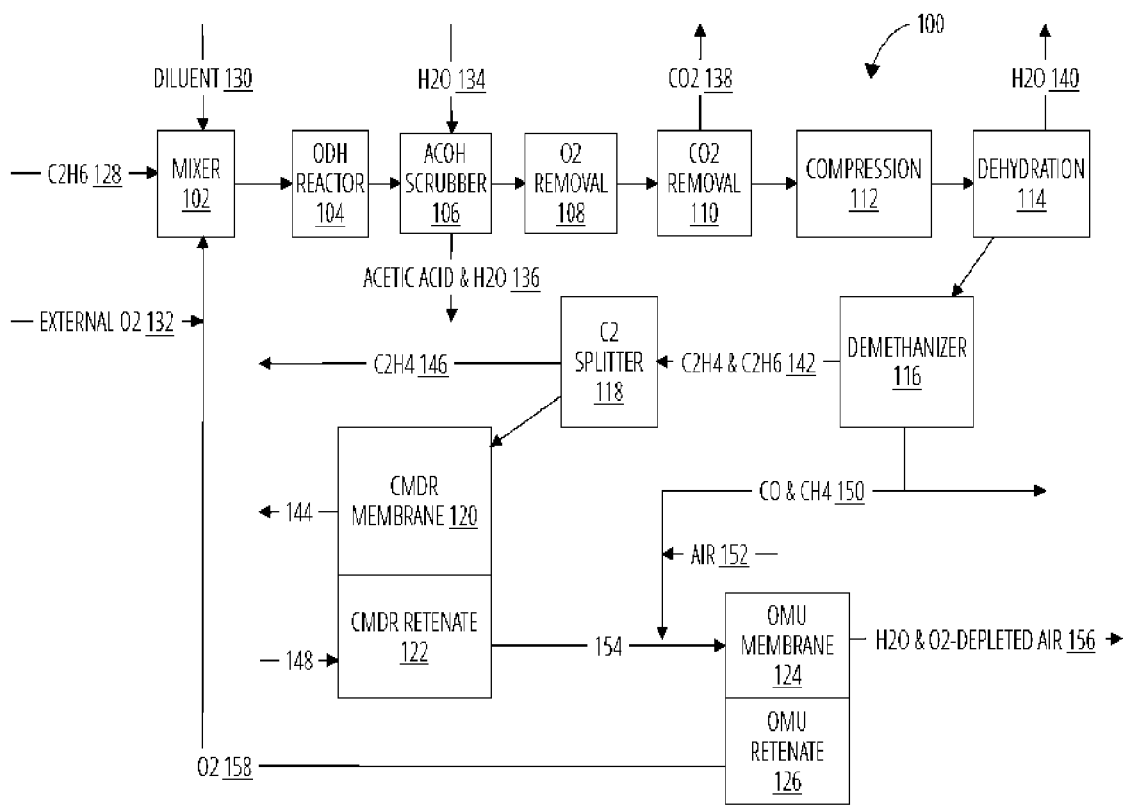
FIG. 1 illustrates an Integrated ODH Process with CMDR Process in accordance with the disclosure.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

As used herein, the term "C2-C4 alkane" refers to one of ethane, propane, n-butane or isobutane, or any combination thereof.

As used herein, the term "C2-C4 alkene" refers to one of ethylene, propylene, α-butylene, cis-β-butylene, trans-β-butylene, isobutylene, or any combination thereof.

As used herein, the term "CMDR" refers to catalytic membrane dehydrogenation reactor.

As used herein, the term "CMEDR" refers to catalyst membrane ethane dehydrogenation reactor.

As used herein, the term "flammability envelope" refers to the envelope defining the flammability zone in mixtures of fuel, oxygen and with or without a heat removal diluent gas.

As used herein, the term "gas hourly space velocity" refers to the ratio of the gas volumetric flow rate where the gas includes the reacting gas species and optionally one or more heat removal diluent gases at standard conditions (i.e., 0° C., 1 bar) to the volume of the catalyst bed. The catalyst bed can refer to either the catalyst active phase, or to the total catalyst formulation which can include such things as catalyst additives or promoters. (abbreviated GHSV)

As used herein, the term "group 4 element" refers to an element from group 4 of the periodic table; the group includes titanium, zirconium and hafnium.

As used herein, the term "group 5 element" refers to an element from group 5 of the periodic table; the group includes vanadium, niobium and tantalum.

As used herein, the term "heat dissipative particles" refers to inert non-catalytic particles that can be used within one or more of the ODH reactors to improve cooling homogeneity and reduction of hot spots in the bed by transferring heat directly to the walls of the reactor.

As used herein, the term "heat removal diluent gas" refers to a gas that dilutes a stream and can remove heat from the stream.

As used herein, the term "mixed metal oxide catalyst" refers to a catalyst that can be used in an oxidative dehydrogenation reactor to oxidatively dehydrogenate a C2-C4 alkane to a C2-C4 alkene.

As used herein, the term "residence time" refers to a measure of how much time material that is flowing through a volume spends in the volume. The residence time in the ODH reactor is equal to the volumetric flow rate of the feed stream divided by the void volume in the reactor.

As used herein, the term "substantially free of hydrogen" refers to a product stream from the disclosed process that contains no hydrogen, undetectable levels of hydrogen, or very low levels of hydrogen that will not affect the end use of the C2-C4 alkene, in many cases ethylene, produced in the process disclosed herein.

As used herein, the term "weight hourly space velocity" refers to the ratio of the gas mass flow rate where the gas includes the reacting gas species and optionally one or more heat removal diluent gases to the mass of the catalyst bed. The catalyst bed can refer to either the catalyst active phase, or to the total catalyst formulation which can include such things as catalyst additives or promoters. (abbreviated WHSV).

A number of patent disclosures are related to various catalyst types including carbon molecular sieves, metal phosphates, and mixed metal oxides. For example, U.S. Pat. Nos. 3,420,911 and 3,420,912 disclose the use of ferrites in the ODH of organic compounds. The ferrites are introduced into a dehydrogenation zone containing the organic compound and an oxidant for a short period, then to a regeneration zone for re-oxidation, and then fed back to the dehydrogenation zone for another cycle.

U.S. Pat. No. 4,536,196 discloses the dehydrogenation of a hydrocarbon in the presence of a hydrogen-permeable membrane including Group 4, 5 and 6 metals which continuously removes hydrogen from the reaction zone. The dehydrogenation of the hydrocarbon under dehydrogenation conditions was at a temperature in the range of 427° C. to 704° C.

U.S. Pat. Nos. 7,329,791 and 8,900,523 disclose a method of converting $C_2$ and/or higher alkanes to olefins by contacting a feedstock containing $C_2$ and/or higher alkanes with a first surface of a metal composite membrane of a sintered homogeneous mixture of an Al oxide or stabilized or partially stabilized Zr oxide ceramic powder and a metal powder of one or more of Pd, Nb, V, Zr, Ta and/or alloys of mixtures thereof. The alkanes dehydrogenate to olefins by contact with the first surface with substantially only atomic hydrogen from the dehydrogenation of the alkanes passing through the metal composite membrane.

U.S. Patent Application Publication No. 2007/0260101 discloses an alkane dehydrogenation process for the production of alkenes in which hydrogen produced in the reaction mixture selectively permeates through a membrane.

WO 2013/135390 A1 discloses a catalyst that could be used for producing olefins from $C_2$-$C_4$ alkanes. The separation of $H_2$ from the reaction using a hydrogen permeable membrane is disclosed, but the nature of the membrane is not specified.

U.S. Patent Application Publication No. 2019/0248717 discloses an oxidative dehydrogenation process including a membrane separation unit to separate an alkene from unreacted alkane in the alkene stream.

The following figures contain references to a particular C2-C4 alkane, ethane, and a particular C2-C4 alkene, ethylene. However, any C2-C4 alkane and C2-C4 alkene could be interchanged with ethane and ethylene.

As shown in FIG. 1, the Integrated ODH Process with CMDR Process 100 includes a mixer 102, an ODH Reactor 104, an AcOH Scrubber 106, an O2 Removal Unit 108, a CO2 Removal Unit 110, Compression Unit 112, Dehydration Unit 114, a Demethanizer Unit 116, a C2 Splitter 118, a CMDR Retenate Side 120 with a second side being a CMDR Membrane side 122, and an OMU Retenate Side 124 with a second side being an OMU Membrane Side 126. The mixer 102 has an inlet stream 128 that includes C2H6, an inlet stream 130 that includes diluent, and an inlet stream that includes oxygen coming both from an External O2 Stream 132, and recycled O2 Stream 158. The AcOH Scrubber 106 has an inlet stream 134 that includes H2O, and an outlet stream 136 that includes Acetic Acid and H2O. The CO2 Removal unit 110 has an outlet stream 138 that includes CO2. The Dehydration unit 114 has an outlet stream 140 that includes H2O. The Demethanizer 116 has an outlet stream 142 that includes C2H4 and C2H6, and an outlet stream 150 that includes CO and CH4 150. The CMDR Retenate Side 120 has an outlet stream 144 that includes ethylene. An outlet from the C2 Splitter 118 also includes ethylene stream 146. Stream 148 can be an inert sweep gas, or a gas containing oxygen such as air, or a mixture of the two. Air can be added via line 152 upstream of the OMU Retenate Side 124, and the outlet can include H2O and O2-Depleted Air in line 156. A stream 154 can include hydrogen if an inert sweep gas was used in stream 148, or reduced oxygen air and water if air is used in stream 148.

Figure 2:
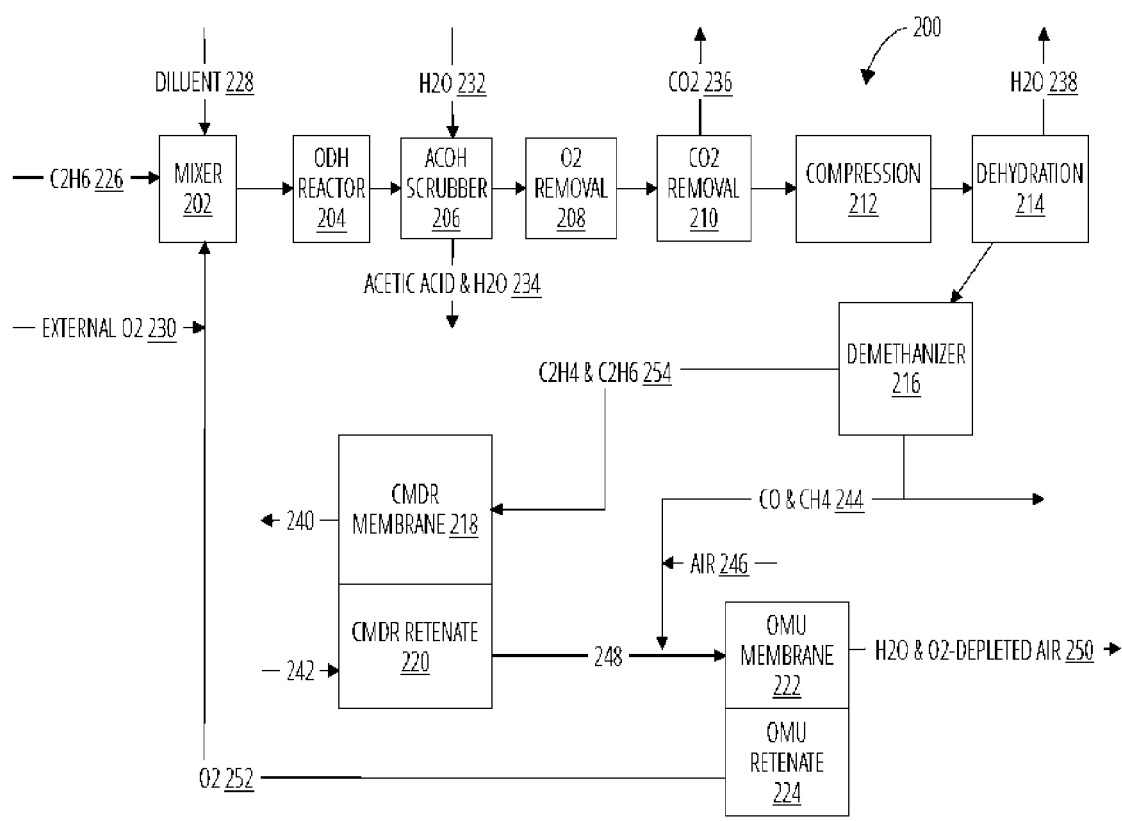
FIG. 2 illustrates an Integrated ODH Process without C2 Splitter with CMDR Process in accordance with the disclosure.

As shown in FIG. 2, the Integrated ODH Process without C2 Splitter with CMDR Process 200 includes a mixer 202, an ODH Reactor 204, an AcOH Scrubber 206, a unit that performs O2 Removal 208, a unit that performs CO2 Removal 210, Compression 212, Dehydration 214, a Demethanizer 216, a CMDR Retenate side 218 with a second side being a CMDR Membrane side 220, and an OMU Retenate side 222 with a second side being an OMU Membrane Side 224. The mixer 202 has an inlet stream that includes C2H6 stream 226, an inlet stream 228 that includes Diluent, and an inlet stream 230 that includes oxygen coming both from an External O2 source and a recycled O2 stream 252. The AcOH Scrubber 206 has an inlet stream 232 that includes H2O, and an outlet stream 234 that includes Acetic Acid and H2O. The CO2 Removal unit 210 has an outlet stream 236 that includes CO2. The Dehydration unit 214 has an outlet stream 238 that includes H2O. The Demethanizer 216 has an outlet stream 254 that includes C2H4 and C2H6, and an outlet stream 244 that includes CO and CH4. The CMDR Retenate side 218 has an outlet stream 240 that includes ethylene. Stream 242 can be an inert sweep gas, or a gas containing oxygen such as air, or a mixture of the two. Air via air stream 246 can be added upstream of the OMU Retenate side 222, and the outlet stream 250 can include H2O and O2-Depleted Air. A stream 248 can include hydrogen if an inert sweep gas was used in stream 242, or reduced oxygen air and water if air is used in stream 242.

Figure 3:
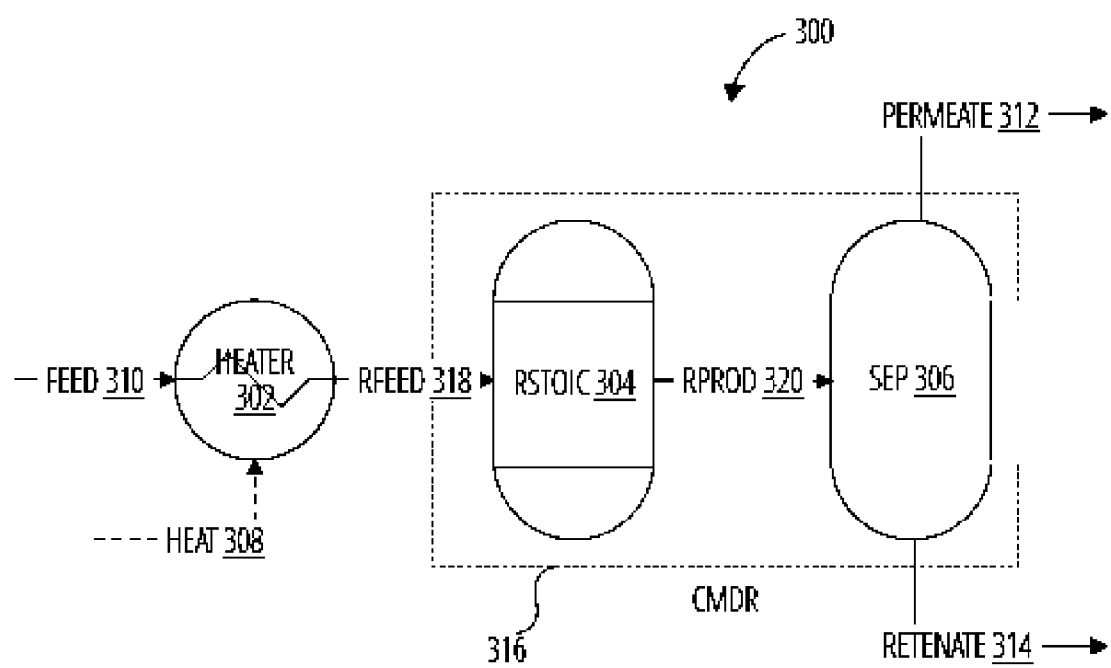
FIG. 3 illustrates a Catalytic Membrane Reactor using Effluent Flow Upstream of a C2 Splitter without Heat Integration in accordance with the disclosure.

As shown in FIG. 3, the Catalytic Membrane Reactor using Effluent Flow Upstream of C2 Splitter without Heat Integration 300 is a block diagram showing the connectivity in an AspenPlus® model (Aspen Technology Inc.) and includes a Heater 302 which has an inlet stream 310 and is heated with Heat supply 308, a stoichiometric reactor (RStoic) 304 and a separator (Sep) 306 which combined model a CMDR 316, with outlet streams Permeate stream 312 and Retenate stream 314.

Figure 4:
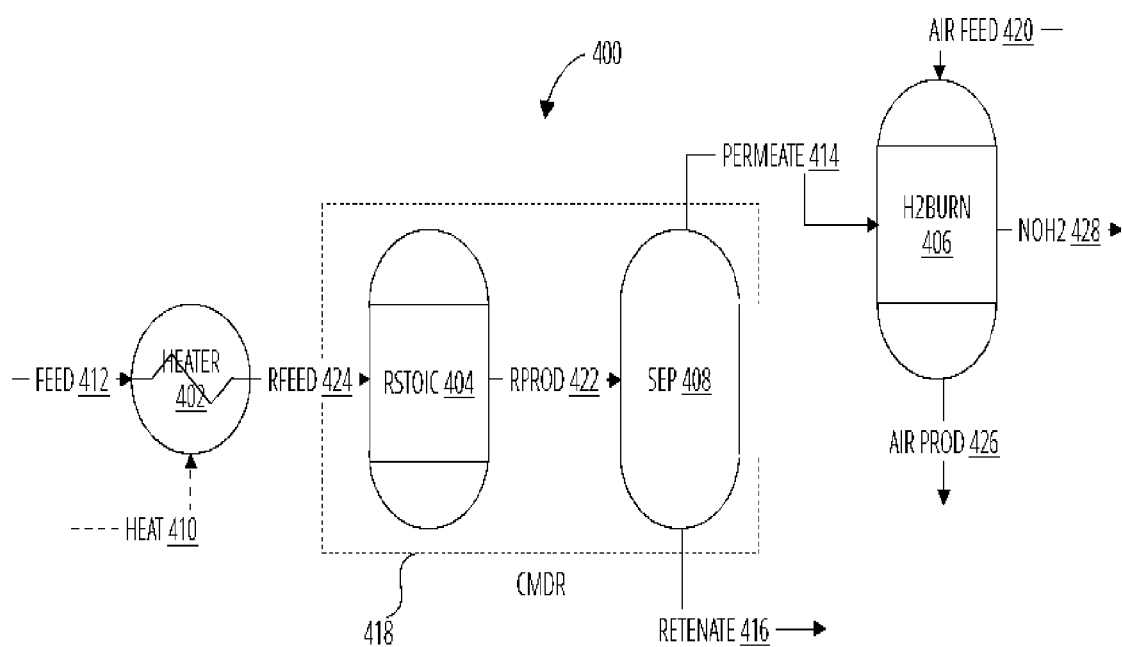
FIG. 4 illustrates a Catalytic Membrane Reactor using Effluent Flow Upstream of a C2 Splitter with Heat Integration in accordance with the disclosure.

As shown in FIG. 4, the Catalytic Membrane Reactor using Effluent Flow Upstream of C2 Splitter with Heat Integration 400 is a block diagram showing the connectivity in an AspenPlus® model and includes a Heater 402 which as an inlet stream Feed 412 and is heated with Heat supply 410, an RStoic 404 and a Sep 408 which combined model a CMDR 418, with outlet streams Permeate stream 414 and Retenate stream 416, the Permeate stream 414, which includes hydrogen is an inlet to a hydrogen burner block (H2Burn) 406, which also has an inlet that includes Air Feed 420.

The ODH Process

Oxidative dehydrogenation (ODH) of C2-C4 alkanes includes contacting a mixture of a C2-C4 alkane and oxygen in one or more ODH reactors with one or more mixed metal oxide catalysts under conditions that promote oxidation of the C2-C4 alkane into its corresponding C2-C4 alkene. Conditions within the reactor are controlled by the operator and include, but are not limited to, parameters such as temperature, pressure, and flow rate. Conditions will vary and can be optimized for a particular C2-C4 alkane, in some embodiments ethane, or for a specific mixed metal oxide catalyst, or whether a heat removal diluent gas or heat dissipative particles are used in the mixing of the reactants.

Any of the known reactor types applicable for the ODH of alkanes may be used with the methods disclosed herein. The methods may be used with conventional fixed bed reactors, fluidized bed reactors, ebulliated bed reactors, rotating bed reactors, swing bed reactors, etc. In a typical fixed bed reactor, reactants are introduced into the reactor at one end, flow past an immobilized catalyst, products are formed and leave at the other end of the reactor. Designing a fixed bed reactor suitable for the methods disclosed herein can follow techniques known for reactors of this type. A person skilled in the art would know which features are required with respect to shape and dimensions, inputs for reactants, outputs for products, temperature and pressure control, and means for immobilizing the catalyst.

The methods may be used with conventional fluidized bed reactors, where the catalyst bed can be supported by a porous structure, or a distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and the reactants are subsequently removed from the upper end of the reactor. A fluidized bed could also be used in a process in which the catalyst is regenerated in a regeneration bed and then returned to the fluidized bed. Design considerations those skilled in the art can modify and optimize include, but are not limited to, the shape of the reactor, the shape and size of the distributor plate, the input temperature, the output temperature, and reactor temperature and pressure control.

Embodiments of the disclosure include using a combination of both fixed bed and fluidized bed reactors, each with the same or different ODH mixed metal oxide catalyst. The multiple reactors can be arrayed in series or in parallel configuration, the design of which falls within the knowledge of the worker skilled in the art.

Use of an ODH reactor for performing an ODH process consistent with the present disclosure falls within the knowledge of the person skilled in the art. For best results, the ODH of a C2-C4 alkane may be conducted at temperatures from 300° C. to 500° C., in some cases from 300° C. to 425° C., in other cases from 330° C. to 400° C., at pressures from 0.5 to 100 psig (3.447 to 689.47 kPag), in some cases from 15 to 50 psig (103.4 to 344.73 kPag), and the residence time, in which the volume of active mixed metal oxide catalyst is in the numerator and the flow rate of feed gas is in the denominator, in the ODH reactor is typically from 0.002 to 30 seconds, in some cases from 1 to 10 seconds.

In some embodiments, the ODH process has a selectivity for the corresponding C2-C4 alkene (ethylene in the case of ethane ODH) of greater than 85%, in some cases greater than 90%. The flow of reactants and heat removal diluent gas can be described in any number of ways known in the art. Typically, flow is described and measured in relation to the volume of all feed gases (reactants and diluent) that pass over the volume of the active catalyst bed in one hour, or gas hourly space velocity (GHSV). The GHSV can range from 500 to 30000 $h^{-1}$, in some cases greater than 1000 $h^{-1}$. The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include heat removal diluent gas added to the gas mixture. When including the weight of diluents, when used, the WHSV may range from 0.5 $h^{-1}$ to 50 $h^{-1}$, in some cases from 1.0 to 25.0 $h^{-1}$.

The flow of gases through the ODH reactor may also be described as the linear velocity of the gas stream (cm/s), which is defined in the art as the flow rate of the gas stream divided by the cross-sectional surface area of the reactor all divided by the void fraction of the mixed metal oxide catalyst bed. The flow rate generally means the total of the volumetric flow rates of all the gases entering the reactor, and is measured where the oxygen and C2-C4 alkane first contact the mixed metal oxide catalyst and at the temperature and pressure at that point. The cross-section of the ODH reactor is also measured at the entrance of the mixed metal oxide catalyst bed. The void fraction of the mixed metal oxide catalyst bed is defined as the volume of voids in the catalyst bed/total volume of the catalyst bed. The volume of voids refers to the voids between catalyst particles and does not include the volume of pores inside the catalyst particles.

The linear velocity can range from 5 cm/sec to 1500 cm/sec, in some cases from 10 cm/sec to 500 cm/sec.

The space-time yield of corresponding C2-C4 alkene (productivity) in g/hour per kg of the mixed metal oxide catalyst should be not less than 100, in some cases greater than 1500, in other cases greater than 3000, and in some instances greater than 3500 at 350° C. to 400° C. It should be noted that the productivity of the mixed metal oxide catalyst will increase with increasing temperature until the selectivity is decreased.

The use of inert non-catalytic heat dissipative particles can be used within one or more of the ODH reactors. The heat dissipative particles can be present within the mixed metal oxide catalyst bed and include one or more non catalytic inert particulates having a melting point at least 30° C., in some embodiments at least 250° C., in further embodiments at least 500° C. above the temperature upper control limit for the reaction; a particle size in range of 0.5 to 75 mm, in some embodiments 0.5 to 15 mm, in further embodiments in range of 0.5 to 8 mm, in further embodiments in the range of 0.5 to 5 mm; and a thermal conductivity of greater than 30 W/mK (watts/meter Kelvin) within the reaction temperature control limits. In some embodiments the particulates are metals and/or metal alloys and compounds having a thermal conductivity of greater than 50 W/mK (watts/meter Kelvin) within the reaction temperature control limits. Non-limiting examples of suitable metals that can be used in these embodiments include, but are not limited to, silver, copper, gold, aluminum, steel, stainless steel, molybdenum, and tungsten. The heat dissipative particles can have a particle size of from about 1 mm to about 15 mm. In some embodiments, the particle size can be from about 1 mm to about 8 mm. The heat dissipative particles can be added to the bed in an amount from 5 to 95 wt. %, in some embodiments from 30 to 70 wt. %, in other embodiments from 45 to 60 wt. % based on the entire weight of the bed. The particles are employed to potentially improve cooling homogeneity and reduction of hot spots in the bed by transferring heat directly to the walls of the reactor. The heat dissipative particles can optionally be pressed or extruded with the mixed metal oxide catalyst active phase.

ODH Catalyst

Any of the mixed metal oxide catalysts used as ODH catalysts known in the art are suitable for use in the methods disclosed herein. Non-limiting examples of suitable oxidative dehydrogenation catalyst include those containing one or more mixed metal oxides selected from:

i) catalysts of the formula:

$$Mo_a N_b Te_c Nb_d Pd_e O_f$$

wherein a, b, c, d, e and f are the relative atomic amounts of the elements Mo, V, Te, Nb, Pd and O, respectively; and when a=1, b=0.01 to 1.0, c=0 to 1.0, d=0 to 1.0, 0≤e≤0.10 and f is a number to at least satisfy the valence state of the metals present in the catalyst;

ii) catalysts of the formula:

$$Ni_g A_h B_i D_j O_f$$

wherein g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the metals in the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_a E_k G_l O_f$$

wherein E is chosen from Ba, Be, Ca, Cr, Mn, Nb, Ta, Ti, Te, V, W and mixtures thereof; chosen from Al, Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of 1 for Co, Ni, Fe and mixtures thereof is less than 0.5; and f is a number to at least satisfy the valence state of the metals in the catalyst;

iv) catalysts of the formula:

$$V_m Mo_n Nb_o Te_p Me_q O_f$$

wherein Me is chosen from Ta, Ti, W, Hf, Zr, Sb and mixtures thereof; m is from 0.1 to 3; n is from 0.5 to 1.5; o is from 0 to 3; p is from 0.001 to 5; q is from 0 to 2; and f is a number to at least satisfy the valence state of the metals in the catalyst;

v) catalysts of the formula:

$$Mo_a V_r X_s Y_t Z_u M_v O_f$$

wherein X is at least one of Nb and Ta; Y is at least one of Sb and Ni; Z is at least one of Te, Ga, Pd, W, Bi and Al; M is at least one of Be, Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst;

vi) a mixed metal oxide having the empirical formula:

$$Mo_{6.5-7.0}V_3 O_d$$

wherein d is a number to at least satisfy the valence of the metals in the catalyst.

vii) a mixed metal oxide having the empirical formula:

$$Mo_{6.25-7.25}V_3 O_d$$

wherein d is a number to at least satisfy the valence of the metals in the catalyst.

An implementation of an ODH catalyst material is a mixed metal oxide having the formula $Mo_1 V_{0.1-1} Nb_{0.1-1} Te_{0.01-0.2} X_{0-0.2} O_f$ wherein X is selected from Pd, Sb, Ba, Al, W, Ga, Bi, Sn, Cu, Ti, Fe, Co, Ni, Cr, Zr, Ca and oxides and mixtures thereof, and f is a number to satisfy the valence state of the metals present in the catalyst.

An implementation of an ODH catalyst material is a mixed metal oxide that includes Mo, V, O, and iron (Fe). The molar ratio of Mo to V can be from 1:0.25 to 1:0.50 or from 1:0.30 to 1:0.45, or from 1:0.30 to 1:0.35, or from 1:0.35 to 1:0.45. The molar ratio of Mo to Fe can be from 1:0.25 to 1:5.5, or from 1:3 to 1:5.5, or from 1:4.25 to 1:4.75, or from 1:4.45 to 1:4.55, or from 1:0.1 to 1:1, or from 1:0.25 to 1:0.75, or from 1:0.4 to about 1:0.6, or about 1:0.4, or about 1:0.6, or from 1:1.3 to 1:2.2, or from 1:1.6 to 1:2.0, or from 1:1.80 to 1:1.90. Further, oxygen is present at least in an amount to satisfy the valence state of the metals present in the catalyst. The catalyst can have at least a portion of the Fe in the catalyst material present as Fe(III). The catalyst can have at least a portion of the Fe in the catalyst material present as amorphous iron. The catalyst can have at least a portion of the Fe in the catalyst material present as an iron oxide, an iron oxide hydroxide, or a combination thereof. The iron oxide can include an iron oxide selected from hematite ($\alpha$-$Fe_2 O_3$), maghemite ($\gamma$-$Fe_2 O_3$), magnetite ($Fe_3 O_4$), or a combination thereof. The iron oxide hydroxide can include an iron oxide hydroxide selected from a goethite, an akageneite, a lepidocrocite, or a combination thereof.

The catalyst can include at least a portion of the iron as a goethite and at least a portion of the iron as a hematite.

An implementation of an ODH catalyst material is a mixed metal oxide having the empirical formula $Mo_1V_{0.25-0.5}O_d$ wherein d is a number to satisfy the valence state of the metals present in the catalyst. The molar ratio of Mo to V can be from 1:0.25 to 1:0.5, or 1:0.3 to 1:0.49.

An implementation of an ODH catalyst material is a mixed metal oxide that includes Mo, V, O, and aluminum (Al). The molar ratio of Mo to V can be from 1:0.1 to 1:0.50, or from 1:0.25 to 1:0.50, or from 1:0.3 to 1:0.49, or from 1:0.30 to 1:0.45, or from 1:0.30 to 1:0.35, or from 1:0.35 to about 1:0.45. The molar ratio of Mo to Al is from 1:1.5 to 1:6.5, or from 1:3.0 to 1:6.5, or from 1:3.25 to 1:5.5.5, or from 1:3.5 to 1:4.1, or from 1:4.95 to 1:5.05, or from 1:4.55 to 1:4.65, or from 1:1.5 to 1:3.5, or from 1:2.0 to 1:2.2, or from 1:2.9 to 1:3.1. Oxygen is present at least in an amount to satisfy the valence state of the metals present in the catalyst. At least a portion of the Al in the catalyst material can be present as an aluminum oxide; the aluminum oxide can be an aluminum oxide hydroxide. The aluminum oxide hydroxide can include an aluminum oxide hydroxide selected from a gibbsite, a bayerite, a boehmite, or a combination thereof. At least a portion of the Al in the catalyst material can be present as gamma alumina.

An implementation of an ODH catalyst material is a mixed metal oxide that includes Mo, V, O, Al, and Fe. The molar ratio of Mo to V can be from 1:0.1 to 1:0.5, or from 1:0.30 to 1:0.45, or from 1:0.30 to 1:0.35, or from 1:0.35 to 1:0.45. The molar ratio of Mo to Al can be from 1:1.5 to 1:6.0. The molar ratio of Mo to Fe can be from 1:0.25 to 5:5. Oxygen is present at least in an amount to satisfy the valence state of the metals present in the catalyst. The molar ratio of Mo to Fe can be from 1:0.1 to 1:1, and the molar ratio of Mo to Al can be from 1:3.5 to 1:5.5. The molar ratio of Mo to Fe can be from 1:0.25 to 1:0.75, and the molar ratio of Mo to Al can be from 1:3.75 to 1:5.25. The molar ratio of Mo to Fe can be from 1:0.35 to 1:0.65, and the molar ratio of Mo to Al can be from 1:3.75 to 1:5.25. The molar ratio of Mo to Fe can be from 1:0.35 to 1:0.45, and the molar ratio of Mo to Al can be from 1:3.9 to 1:4.0. The molar ratio of Mo to Fe can be from 1:0.55 to 0:65, and the molar ratio of Mo to Al can be from 1:4.95 to 1:5.05. The molar ratio of Mo to Fe can be from 1:1.3 to 1:2.2, and the molar ratio of Mo to Al can be from 1:2.0 to 1:4.0. The molar ratio of Mo to Fe can be from 1:1.6 to 1:2.0, and the molar ratio of Mo to Al can be from 1:2.5 to 1:3.5. The molar ratio of Mo to Fe can be from 1:1.80 to 1:1.90, and the molar ratio of Mo to Al can be from 1:2.9 to 1:3.1. At least a portion of the Fe in the catalyst material can be present as Fe(III). At least a portion of the Fe in the catalyst material can be present as amorphous Fe. At least a portion of the Fe in the catalyst material can be present as an iron oxide, an iron oxide hydroxide, or a combination thereof. In some embodiments, the iron oxide includes an iron oxide selected from hematite ($\alpha$-$Fe_2O_3$), maghemite ($\gamma$-$Fe_2O_3$), magnetite ($Fe_3O_4$), or a combination thereof. Iron oxide hydroxide can include an iron oxide hydroxide selected from a goethite, an akageneite, a lepidocrocite, or a combination thereof. At least a portion of the Fe in the catalyst material can be present as a goethite and at least a portion of the Fe in the catalyst material can be present a hematite. At least a portion of the Al in the catalyst material can be is present as an aluminum oxide. The aluminum oxide can include an aluminum oxide hydroxide. The aluminum oxide hydroxide can include an aluminum oxide hydroxide selected from a gibbsite, a bayerite, a boehmite, or a combination thereof. At least a portion of the aluminum in the catalyst material can be present as a gamma alumina.

An implementation of an ODH catalyst material is a mixed metal oxide that includes Mo, V, Be, and O. The molar ratio of Mo to V can be from 1:0.25 to 1:0.65, or from 1:0.35 to 1:0.55, or from 1:0.38 to 1:0.48. The molar ratio of Mo to Be can be from 1:0.25 to 1:0.85, or from 1:0.35 to 1:0.75, or from 1:0.45 to 1:0.65. Oxygen is present at least in an amount to satisfy the valence state of the metals present in the catalyst.

An implementation of an ODH catalyst material is a mixed metal oxide that includes Mo, V, Be, Al and O. The molar ratio of Mo to V can be from 1:0.25 to 1:0.65, or from 1:0.35 to 1:0.55, or from 1:0.38 to 1:0.48. The molar ratio of Mo to Be can be from 1:0.25 to 1:1.7, or from 1:0.35 to 1:0.75, or from 1:0.45 to 1:0.65. The molar ratio of Mo to Al can be from 1:1 to 1:9, or from 1:2 to 1:8, or from 1:4 to 1:6. Oxygen is present at least in an amount to satisfy the valence state of the metals present in the catalyst. At least a portion of the aluminum in the catalyst material can be present as an aluminum oxide. The aluminum oxide can include an aluminum oxide hydroxide. The aluminum oxide hydroxide can include an aluminum oxide hydroxide selected from a gibbsite, a bayerite, a boehmite, or a combination thereof. At least a portion of the aluminum in the catalyst material can be present as gamma alumina.

An implementation of an ODH catalyst material has an amorphous phase of from 20 wt. % to 50 wt. %, or from 25 wt. % to 45 wt. %, or from 45 wt. % to 75 wt. %, or from 55 wt. % to 65 wt. %, or from 50 wt. % to 85 wt. %, or from 55 wt. % to 75 wt. %, or from 60 wt. % to 70 wt. %.

An implementation of an ODH catalyst material has an average crystallite size of greater than 50 nm, or greater than 75 nm, or greater than 100 nm, or greater than 125 nm, or from 75 nm to 150 nm, or from 75 nm to 250 nm, or from 125 nm to 175 nm.

An implementation of an ODH catalyst material has a mean particle size from 0.5 μm to 10 μm, or from 2 μm to 8 μm, or from 3 μm to 5 μm, or from 0.5 μm to 20 μm, or from 5 μm to 15 μm, or from 7 μm to 11 μm.

An implementation of an ODH catalyst material is characterized by having at least one or more XRD diffraction peaks (2θ degrees) chosen from 6.5±0.2, 7.8±0.2, 8.9±0.2, 10.8±0.2, 13.2±0.2, 14.0±0.2, 22.1±0.2, 23.8±0.2, 25.2±0.2, 26.3±0.2, 26.6±0.2, 27.2±0.2, 27.6±0.2, 28.2±0.2, 29.2±0.2, 30.5±0.2, and 31.4±0.2 wherein the XRD is obtained using CuKα radiation. An implementation of an ODH catalyst material is characterized by having at least one or more XRD diffraction peaks (2θ degrees) chosen from 6.6±0.2, 6.8±0.2, 8.9±0.2, 10.8±0.2, 13.0±0.2, 22.1±0.2, 26.7±0.2, 27.2±0.2, and 28.2±0.2, wherein the XRD is obtained using CuKα radiation.

An implementation of an ODH catalyst material can include from about 0.8 wt. % to about 30 wt. % calcium. The catalyst material can include about 0.15 wt. % to about 2.8 wt. % calcium. The catalyst material can include 0.5 wt. % to 75 wt. % calcium carbonate. The catalyst material can include 5 wt. % to 15 wt. % calcium carbonate.

The catalyst may be supported on or agglomerated with a binder, carrier, diluent or promoter. Some binders include acidic, basic or neutral binder slurries of $TiO_2$, $ZrO_2$, $Al_2O_3$, AlO(OH) and mixtures thereof. Another useful binder includes $Nb_2O_5$. The agglomerated catalyst may be extruded in a suitable shape (rings, spheres, saddles, etc.) of a size typically used in fixed bed reactors. When the catalyst is extruded, various extrusion aids known in the art can be used. In some cases, the resulting support may have a cumulative surface area of as high as 300 m$^2$/g as measured by BET, in some cases less than 35 m$^2$/g, in some cases, less than 20 m$^2$/g, in other cases, less than 3 m$^2$/g, and a cumulative pore volume from 0.05 to 0.50 cm$^3$/g.

The catalysts may be alone or in combination. Also, in some embodiments the catalysts may be used with a promotor such ad Bi, Be, Nb, Ta, Ti, Pd, Pt, Re or Ru to increase the catalyst activity.

The mixed metal oxide catalyst can be a supported catalyst. The support may be selected from oxides of titanium, zirconium, aluminum, magnesium, yttrium, lanthanum, silicon, zeolites and clays and their mixed compositions or a carbon matrix. The mixed metal oxide catalyst can also have a binder added which increases cohesion among the catalyst particles and optionally improves adhesion of the catalyst to the support if present. The mixed metal oxide catalyst can be diluted with inert material, such as DENSTONE® 99 (Saint-Gobain Ceramics & Plastics, Inc.) alumina particles or corrosion resistant steels such as SS 316 particles.

Oxygen/Alkane Mixture

Mixtures of one or more C2-C4 alkanes (shown as C2H6 stream 128 in FIGS. 1 and C2H6 stream 226 in FIG. 2) with oxygen (shown as O2 stream 158 and External O2 stream 132 in FIGS. 1 and O2 stream 252 and External O2 stream 230 in FIG. 2) can be employed using ratios that fall outside of the flammability envelope of the one or more C2-C4 alkanes and oxygen. The ratio of C2-C4 alkane to oxygen may fall outside the upper flammability envelope; in these cases, the percentage of oxygen in the mixture can be less than 30 vol. %, in some cases less than 25 vol. %, or in other cases less than 20 vol. %.

In cases with higher oxygen percentages, C2-C4 alkane percentages can be adjusted to keep the mixture outside of the flammability envelope. While a person skilled in the art would be able to determine an appropriate ratio level, in many cases the percentage of C2-C4 alkane is less than about 40 vol. %. As a non-limiting example, where the mixture of gases prior to the ODH process includes 10 vol. % oxygen and 15 vol. % C2-C4 alkane, the balance can be made up with a heat removal diluent gas. Non-limiting examples of useful heat removal diluent gas in this embodiment include, but are not limited to, one or more of nitrogen, carbon dioxide, and steam. In some embodiments, the heat removal diluent gas should exist in the gaseous state at the conditions within the reactor and should not increase the flammability of the hydrocarbon added to the reactor, characteristics that a skilled worker would understand when deciding on which heat removal diluent gas to employ. The heat removal diluent gas can be added to either of the C2-C4 alkane containing gas or the oxygen containing gas or to both gases prior to entering the ODH reactor or may be added directly into the ODH reactor.

In some embodiments mixtures that fall within the flammability envelope may be employed, as a non-limiting example, in instances where the mixture exists in conditions that prevent propagation of an explosive event. In these non-limiting examples, the flammable mixture is created within a medium where ignition is immediately quenched. As a further non-limiting example, a user may design a reactor where oxygen and the one or more C2-C4 alkanes are mixed at a point where they are surrounded by a flame arresting material. Any ignition would be quenched by the surrounding material. Flame arresting materials include, but are not limited to, metallic or ceramic components, such as stainless steel walls or ceramic supports. In some embodiments, oxygen and C2-C4 alkane can be mixed at a low temperature, where an ignition event would not lead to an explosion, then introduced into the reactor before increasing the temperature. Flammable conditions may not exist when the mixture is surrounded by the flame arrestor material inside of the reactor.

Carbon Monoxide Output

Carbon monoxide can be produced in the ODH reaction as a by-product of oxidation of the one or more C2-C4 alkanes. The carbon monoxide output is a function of the amount of carbon monoxide produced in the oxidative process.

Measuring the amount of carbon monoxide coming off the ODH reactor can be done using any means known in the art. For example, one or more detectors such as GC, IR, or Rahman detectors, are situated immediately downstream of the reactor to measure the carbon monoxide output. While not required, the output of other components may also be measured. These include but are not limited to the amounts of ethylene, unreacted ethane, carbon dioxide and oxygen, and by-products such as acetic acid.

Carbon monoxide output can be stated using any metric commonly used in the art. For example, the carbon monoxide output can be described in terms of mass flow rate (g/min) or volumetric flow rate (cm$^3$/min). In some embodiments, normalized selectivity can be used to assess the degree to which carbon monoxide is produced or consumed. In that instance the net mass flow rate of CO (i.e. the difference between the mass flow rate of CO leaving the ODH reactor and the mass flow rate of CO entering the reactor) is normalized to the conversion of ethane, in essence describing what fraction of ethane is converted into carbon monoxide as opposed to ethylene, or other by-products such as acetic acid.

Many industrial processes, in addition to ODH, produce carbon monoxide which must be captured or flared where it contributes to the emission of greenhouse gases. Using the carbon monoxide mitigation steps disclosed herein converts most, if not all, carbon monoxide resulting from the ODH process to carbon dioxide. An advantage then is the ability to reduce or eliminate the amount of carbon monoxide produced in the ODH process in combination with other processes, such as thermal cracking.

Acetylene Output

Acetylene can be produced in the ODH reaction as a by-product of oxidation of the one or more C2-C4 alkanes. The acetylene output is a function of the amount of acetylene produced in the oxidative process.

Measuring the amount of acetylene coming off the ODH reactor can be done using any means known in the art. For example, one or more detectors such as GC, IR, or Rahman detectors, are situated immediately downstream of the reactor to measure the acetylene output. While not required, the output of other components may also be measured. These include but are not limited to the amounts of ethylene, unreacted ethane, carbon monoxide, carbon dioxide and oxygen, and by-products such as acetic acid.

Acetylene output can be stated using any metric commonly used in the art. For example, the acetylene output can be described in terms of mass flow rate (g/min), volumetric flow rate (cm$^3$/min) or volumetric parts per million (ppmv). In some embodiments, normalized selectivity can be used to assess the degree to which acetylene is produced or consumed. In that instance the net mass flow rate of acetylene (i.e. the difference between the mass flow rate of acetylene leaving the ODH reactor and the mass flow rate of acetylene entering the reactor) is normalized to the conversion of ethane, in essence describing what fraction of ethane is converted into acetylene as opposed to ethylene, or other by-products such as acetic acid.

Using the acetylene mitigation steps disclosed herein reacts most, if not all, acetylene resulting from the ODH process. An advantage then is the ability to reduce or eliminate the amount of acetylene produced in the ODH process in combination with other processes, such as thermal cracking and eliminate downstream unit operations in an ODH-type process.

Addition of Steam

The amount of steam added to the ODH process affects the degree to which carbon dioxide acts as an oxidizing agent. In some embodiments steam may be added directly to the ODH reactor, or steam may be added to the individual reactant components (i.e. the C2-C4 alkane, oxygen, or heat removal diluent gas) or combinations thereof, and subsequently introduced into the ODH reactor along with one or more of the reactant components. Alternatively, steam may be added indirectly as water mixed with either the C2-C4 alkane, oxygen or heat removal diluent gas, or a combination thereof, with the resulting mixture being preheated before entering the reactor. When adding steam indirectly as water the preheating process should increase the temperature so that the water is entirely converted to steam before entering the reactor.

Increasing the amount of steam added to a reactor increases the degree to which carbon dioxide acts as an oxidizing agent. Decreasing the amount of steam added to the reactor decreases the degree to which carbon dioxide acts as an oxidizing agent. In some embodiments a user monitors the carbon dioxide output and compares it to a predetermined target carbon dioxide output. If the carbon dioxide output is above the target a user can then increase the amount of steam added to the ODH process. If the carbon dioxide output is below the target a user can decrease the amount of steam added to the ODH process, provided steam has been added. Setting a target carbon dioxide output level is dependent on the requirements for the user. In some embodiments increasing the steam added will have the added effect of increasing the amount of acetic acid and other by-products produced in the process. A user that is ill-equipped to separate out larger amounts of acetic acid from the output of the ODH process may instead reduce steam levels to a minimum, while a user that desires a process that consumes carbon dioxide may choose to maximize the amount of steam that can be added. The amount of steam added to the one or more ODH reactors can be up to about 40 wt. %, in some cases up to about 35 wt. %, in other cases up to about 30 wt. %, and in some instances up to about 25 wt. %.

In some embodiments when using two or more ODH reactors a user may choose to control carbon dioxide output in only one, or less than the whole complement of reactors. For example, a user may opt to maximize carbon dioxide output of an upstream reactor so that the higher level of carbon dioxide can be part of the heat removal diluent gas for the subsequent reactor. In that instance, maximizing carbon dioxide output upstream minimizes the amount of heat removal diluent gas that would need to be added to the stream prior to the next reactor.

There is no requirement for adding steam to an ODH process, as it is one of many alternatives for the heat removal diluent gas. For processes where no steam is added, the carbon dioxide output is maximized under the conditions used with respect to ethane, oxygen and heat removal diluent gas inputs. Decreasing the carbon dioxide output is then a matter of adding steam to the reaction until carbon dioxide output drops to the desired level. In embodiments where oxidative dehydrogenation conditions do not include addition of steam, and the carbon dioxide output is higher than the desired carbon dioxide target level, steam may be introduced into the reactor while keeping relative amounts of the main reactants (i.e. C2-C4 alkane and oxygen) and heat removal diluent gas added to the reactor constant, and monitoring the carbon dioxide output, increasing the amount of steam until carbon dioxide decreases to the target level.

In some embodiments, a carbon dioxide neutral process is achieved by increasing steam added so that any carbon dioxide produced in the ODH process can then be used as an oxidizing agent such that there is no net production of carbon dioxide. Conversely, if a user desires net positive carbon dioxide output then the amount of steam added to the process is reduced or eliminated to maximize carbon dioxide production. As the carbon dioxide levels increase there is potential to reduce oxygen consumption, as carbon dioxide is competing as an oxidizing agent. The skilled person would understand that using steam to increase the degree to which carbon dioxide acts as an oxidizing agent can impact oxygen consumption. The implication is that a user can optimize reaction conditions with lower oxygen contributions, which may assist in keeping mixtures outside of flammability limits.

In embodiments of the disclosure, the stream exiting the one or more ODH reactors is treated to remove or separate water and water-soluble hydrocarbons from the stream exiting the one or more ODH reactors, such as in the steps AcOH Scrubber 106 in FIG. 1 and AcOH Scrubber 206 in FIG. 2. In particular embodiments, this stream is fed to a CO Oxidation reactor.

Acetic Acid Removal

Prior to being fed to a CO Oxidation Reactor (shown as O2 Removal 108 in FIGS. 1 and O2 Removal 208 in FIG. 2), the stream exiting the one or more ODH reactors is directed to quench tower or acetic acid scrubber, as shown as AcOH Scrubber 106 in FIG. 1 and AcOH Scrubber 206 in FIG. 2, which facilitates removal of oxygenates, such as acetic acid, ethanol, and water via a bottom outlet. A stream containing unconverted C2-C4 alkane (such as ethane), corresponding C2-C4 alkene (such as ethylene), unreacted oxygen, carbon dioxide, carbon monoxide, optionally acetylene and heat removal diluent gas, are allowed to exit the scrubber and are fed to the CO Oxidation Reactor.

The oxygenates removed via the quench tower or acetic acid scrubber can include carboxylic acids (for example acetic acid), aldehydes (for example acetaldehyde), alcohol (for example ethanol) and ketones (for example acetone), shown as Acetic Acid and $H_2O$ stream 136 in FIG. 1 and Acetic Acid and H2O stream 234 in FIG. 2. The amount of oxygenate compounds remaining in the stream exiting the scrubber and fed to the CO Oxidation Reactor will often be zero, i.e. below the detection limit for analytical test methods typically used to detect such compounds. When oxygenates can be detected they can be present at a level of up to about 1 per million by volume (ppmv), in some cases up to about 5 ppmv, in other cases less than about 10 ppmv, in some instances up to about 50 ppmv and in other instances up to about 100 ppmv and can be present up to about 1,000 ppmv, in some cases up to about 1 vol. %, in other cases up to about 2 vol. %. The amount of oxygenates or acetic acid in the stream exiting the scrubber and fed to the CO Oxidation Reactor can be any value, or range between any of the values recited above.

Amine Wash

A separation method applicable for use with the present disclosure is the use of alkylamines, referred to herein as amines, in a scrubber to remove carbon dioxide from gaseous compositions, as shown as CO2 Removal 110 in FIG. 1 and CO2 Removal 210 in FIG. 2. Carbon dioxide present in a gas can be absorbed by an aqueous amine solution, which can then be separated from the remaining gaseous components. The amine containing solution can be stripped of carbon dioxide by heating the solution above 100° C. and recycling to continue the process. Water from the stripper vapor can be condensed, leaving relatively pure carbon dioxide. The carbon dioxide, which is typically highly concentrated, can be captured and sold, or, alternatively it can be recycled back to act as a heat removal diluent gas for the C2-C4 alkane and oxygen containing gases when introduced into the ODH reactor. Carbon dioxide produced in the process can be captured instead of being flared where it contributes to greenhouse gas emissions.

Consideration of the type of amines used in the process requires special attention. The particular amines that are used vary in their ability to remove oxygen and in their tendency to promote the formation of degradation products. As a non-limiting example, monoethanolamine (MEA) is commonly used and is capable of removing a high percentage of carbon dioxide, even at low concentrations, but can also react with the carbon dioxide to form degradation products. This results in lower carbon dioxide capture and a reduction of available amines for subsequent absorption cycles.

The Oxygen Removal Reactor

Oxygen can be removed from the process stream by, as non-limiting examples, removal or by reaction. An example of an oxygen separation module, as shown as OMU Retenate side 124 in FIG. 1 and OMU Retenate side 222 in FIG. 2, is a sealed vessel with two compartments, separated by a temperature dependent oxygen transport membrane. The two compartments are the retentate side and the permeate side. That the membrane is temperature dependent means that at a critical temperature the membrane will selectively allow oxygen to pass through from one side to the other. The oxygen separation module also includes at least two inlets, an air input for introducing atmospheric air into the retentate side and an overhead stream into either of the retentate side or the permeate side, or both retentate and permeate sides. Finally, there are two outputs from the oxygen separation module, an exhaust for removal of oxygen depleted air ($H_2O$ and O2-Depleted Air stream 156 in FIGS. 1 and H2O and O2-Depleted Air stream 250 in FIG. 2) and combustion products from the retentate side, and an outlet for removal of oxygen enriched gas (O2 stream 158 in FIGS. 1 and O2 stream 252 in FIG. 2) and possibly combustion products from the permeate side. The oxygen enriched gas, and possibly combustion products, may be recycled back as or part of the oxygen containing gas introduced into the ODH reactor.

The oxygen flux across the membrane is dependent upon the thickness of the membrane. A thin membrane allows oxygen to cross more quickly than a thick membrane. A membrane that includes a single layer, or monolithic type membrane, may be reduced in thicknesses in the range of 0.1 to 0.2 µm to allow greater oxygen flux. However, these thicknesses are not practical due to susceptibility to mechanical instability. If a monolithic membrane is to be used, thicknesses below 0.2 mm are not recommended. Other known membrane configurations include asymmetric membranes where a very thin conducting layer is supported on both sides by a porous structure. This allows a user to employ very thin membranes that allow higher oxygen flux without sacrificing stability. It is not essential to use any particular membrane structure provided the oxygen flux across the membrane is sufficient. In the present disclosure the oxygen transport membrane has an oxygen flux within the range of 300 to 1500 l/hr*$m^2$, more in some cases from 500 to 1300 l/hr*$m^2$, and in other cases from 700 to 1000 l/hr*$m^2$.

Oxidation of Carbon Monoxide

Oxygen can also be removed reacting it with carbon monoxide to form carbon dioxide. In this instance, the ODH reactor product stream is fed to a CO Oxidation reactor (shown as O2 Removal 108 in FIGS. 1 and O2 Removal 208 in FIG. 2), which contains a catalyst that includes one or more selected from a group 11 metal, a group 4 metal, a group 7, a group 9 metal, a lanthanide metal, and an actinide metal and/or their corresponding metal oxides capable of converting at least a portion of the carbon monoxide to carbon dioxide. The carbon dioxide can be recycled to the ODH reactor as described herein.

In embodiments of the disclosure, the group 11 metal can be selected from copper, silver, gold and combinations thereof. In certain embodiments of the disclosure, the group 11 metal is silver or copper.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 7 metal can be selected from manganese, technetium, rhenium, bohrium and combinations thereof. In certain embodiments of the disclosure, the group 7 metal is manganese.

In embodiments of the disclosure, the group 9 metal can be selected from cobalt, rhodium, iridium, meitnerium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, Ho, Er, Tm, Yb and combinations thereof. In certain embodiments of the disclosure, the lanthanide metal is cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the CO Oxidation reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments, the promoter includes cerium and its corresponding metal oxides.

In embodiments of the disclosure, the CO Oxidation reactor catalyst, in some cases a group 11 metal, and optional promotor are provided on a support. The support is typically an inert solid with a high surface area, to which the CO Oxidation reactor catalyst and optional promotor can be affixed. In many embodiments, the support includes Si, Ge, Sn, their corresponding oxides and combinations thereof.

In embodiments of the disclosure, non-limiting examples of suitable CO Oxidation reactor catalysts with optional promotors and supports include $Ag/SiO_2$, $AgCeO_2/SiO_2$, AgZrO$_2$/SiO$_2$, AgCo$_3$O$_4$/SiO$_2$, Cu/SiO$_2$, CuCeO$_2$/SiO$_2$, CuZrO$_2$/SiO$_2$, CuCo$_3$O$_4$/SiO$_2$ and combinations thereof.

In other embodiments of the disclosure, non-limiting examples of suitable CO Oxidation reactor catalysts with optional promotors and supports include AgCeO$_2$/SiO$_2$, AgZrO$_2$/SiO$_2$ and combinations thereof.

In specific embodiments of the disclosure, the CO Oxidation reactor catalyst includes silver, the optional promoter includes cerium and the support includes SiO$_2$.

In specific embodiments of the disclosure, the CO Oxidation reactor catalyst includes copper, the optional promoter includes cerium and the support includes SiO$_2$.

In specific embodiments of the disclosure, when oxidation of carbon monoxide is desired, the CO Oxidation reactor catalyst includes manganese, the optional promoter includes cerium and the support includes SiO$_2$.

Acetylene Oxidation

Another non-limiting example of a reaction that can remove oxygen is oxidation of acetylene. In this non-limiting example, the ODH reactor product stream is fed to the CO Oxidation reactor (shown as O2 Removal 108 in FIGS. 1 and O2 Removal 208 in FIG. 2), which contains a catalyst that includes one or more selected from a group 11 metal, a group 4 metal, a group 9 metal, a lanthanide metal, and an actinide metal and/or their corresponding metal oxides capable of reacting at least a portion of the acetylene.

In embodiments of the disclosure, the group 11 metal can be selected from copper, silver, gold and combinations thereof. In certain embodiments of the disclosure, the group 11 metal is silver.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 9 metal can be selected from cobalt, rhodium, iridium, meiternium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, Ho, Er, Tm, Yb and combinations thereof. In certain embodiments of the disclosure, the lanthanide metal is Cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the CO Oxidation reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments, the promoter includes cerium and its corresponding metal oxides.

In embodiments of the disclosure, the CO Oxidation reactor catalyst, in some cases a group 11 metal, and optional promotor are provided on a support. The support is typically an inert solid with a high surface area, to which the CO Oxidation reactor catalyst and optional promotor can be affixed. In many embodiments, the support includes Si, Ge, Sn, their corresponding oxides and combinations thereof.

In embodiments of the disclosure, non-limiting examples of suitable CO Oxidation reactor catalysts with optional promotors and supports include Ag/SiO$_2$, AgCeO$_2$/SiO$_2$, AgZrO$_2$/SiO$_2$, AgCo$_3$O$_4$/SiO$_2$, Cu/SiO$_2$, CuCeO$_2$/SiO$_2$, CuZrO$_2$/SiO$_2$, CuCo$_3$O$_4$/SiO$_2$ and combinations thereof.

In other embodiments of the disclosure, non-limiting examples of suitable CO Oxidation reactor catalysts with optional promotors and supports include AgCeO$_2$/SiO$_2$, AgZrO$_2$/SiO$_2$ and combinations thereof.

Caustic Wash Tower

A "caustic wash tower", "scrubber" or "wet scrubber" is typically a large-scale treatment unit that performs a continuous wash by spraying the ODH process stream with a caustic absorption liquid. As a non-limiting example, the caustic wash tower can be used to purify the ODH process stream to remove, as non-limiting examples, acid gases such as hydrogen sulphide (H$_2$S) and carbon dioxide (CO$_2$). A caustic wash tower could optionally be placed after the amine wash, or a caustic wash could be part of the CO2 Removal 110 in FIG. 1 or CO2 Removal 210 in FIG. 2.

Demethanizer Distillation Tower

The demethanizer distillation tower (shown as Demethanizer 116 in FIG. 1 and Demethanizer 216 in FIG. 2) typically includes a cryogenic distillation column. The distillate is a combination of methane and lighter gases, that can include hydrogen, CO, and nitrogen gas. The remaining liquid includes higher hydrocarbons.

C2/C2+ Distillation Tower

It is well known that the degree of separation capable within a distillation tower is dependent upon the number of trays within the unit. The most common method involves cryogenic distillation, so the nature of the species targeted for separation and their relative volatilities plays a role. For example, the relative volatility of ethylene to ethane is quite small. As a result, a tower designed to separate the two species needs to be tall and include a large number of trays. The C2/C2+ hydrocarbons can be directed to a C2+ splitter (C2 Splitter 118 in FIG. 1) to separate the C2-C4 alkane from its corresponding C2-C4 alkene. The C2-C4 alkane can be fed back to the ODH reactor, and the corresponding C2-C4 alkene, the target product, can be captured and employed for use in a variety of applications that depend on the nature of the C2-C4 alkene. For example, if the desired product is ethylene then use in synthesis of polyethylene would be appropriate.

CMDR Reactor

The catalytic membrane dehydrogenation reactor (CMDR) or reactors includes at least one H$_2$ membrane containing at least one group 4 element and at least one group 5 element and can be constructed in tubular or planar form. The reactor also includes at least one ODH catalyst for converting C2-C4 alkane to C2-C4 alkene. The membrane can enhance the C2-C4 alkane to C2-C4 alkene reaction conversion while permeating the hydrogen gas produced.

The group 4 element can be selected from Ti, Zr and Hf.

The group 5 element can be selected from V, Nb and Ta.

In embodiments of this disclosure, the CMDR can be used to convert ethane to ethylene, and in this case can be called a catalytic membrane ethane dehydrogenation reactor, or CMEDR. A are examples of CMDRs are shown in FIG. 1 as CMDR Retenate 120 and CMDR Membrane 122, FIG. 2 as CMDR Retenate 218 and CMDR Membrane 220, FIG. 3 as CMDR 316 and FIG. 4 as CMDR 418.

The H$_2$ membrane can provide highly selective catalytic removal of H$_2$ from mixtures containing combinations of C2-C4 alkane, C2-C4 alkene, CO, CO$_2$, and H$_2$O mixture at elevated pressure. The pressure in this instance can be at least about 5, in some cases at least about 7 and in other cases at least about 10 barg and can be up to about 35, in some cases up to about 30 and in other cases up to about 25 barg. The pressure in the CMDR reactor can be any value or range between the values recited above.

The $H_2$ membrane is activated at operating temperature of at least about 325° C., in some cases at least about 340° C. and in other cases at least about 350° C. and can be activated at an operating temperature of up to about 440° C., in some cases up to about 425° C. and in other cases up to about 410° C. The operating temperature to activate the membrane in the CMDR reactor can be any value or range between the values recited above.

Operation of the CMDR process involves passing the product stream to a catalytic membrane dehydrogenation reactor process that includes at least one membrane containing one or more group 4 elements or group 5 elements to dehydrogenate at least a portion of the unreacted C2-C4 alkane to produce at least one permeate stream that includes hydrogen and at least one retentate stream that includes one or more corresponding C2-C4 alkenes that is substantially free of hydrogen.

At least one membrane in the catalytic membrane dehydrogenation reactor process can be an ionic membrane.

At least one membrane in the catalytic membrane dehydrogenation reactor process can contain at least one of Ti, Zr, Hf, V, Nb or Zr.

At least one membrane in the catalytic membrane dehydrogenation reactor process can contain at least one of Nb, Ta, V, or Zr.

In embodiments of this disclosure, the membrane material can be used as part of a CMDR reactor integrated downstream of many of the unit operations described above.

In many embodiments of the disclosure, the integrated CMEDR reactor increases one pass ethylene yield in the processes according to this disclosure to convert most or all unreacted ethane to ethylene.

In some embodiments, as explained herein, the integrated CMDR reactor can access all or a portion of the heat required to activate the $H_2$ membrane from the ODH heat of reaction and/or combustion of the $H_2$ generated through the use of the $H_2$ membrane.

In some embodiments, as explained herein, if an $O_2$ membrane unit is used, the ODH heat of reaction and/or combustion of the $H_2$ generated through the use of the $H_2$ membrane can provide all or a portion of the heat required to activate the $O_2$ membrane unit.

The Integrated Process

Industrially the reaction can be carried out in a series of sequential reactors and/or separation zones.

The two block flow diagrams, FIG. 1 and FIG. 2, represent the integration of a CMDR process, in the block diagrams shown as a CMEDR process, downstream of the ODH process. In these block flow diagrams, it was assumed that the $O_2$ stream required for the ODH process can be provided by the $O_2$ membrane unit (OMU Retenate side 124 and OMU Membrane side 126 in FIG. 1 and OMU Retenate side 222 and OMU Membrane side 224 in FIG. 2) and/or External O2 (External O2 stream 132 in FIG. 1 and External O2 stream 230 in FIG. 2), which can come from other units such as a pressure swing absorption unit, or a cryogenic unit, etc.

It is noteworthy that the CMDR reactor could become poisoned by $H_2S$. Placing this unit downstream of the ODH process as shown in the block flow diagrams would eliminate the chance of membrane poisoning due to clean feed gas stream to the membrane unit.

In an embodiment, the heat integration between the CMDR reactor, OMU and ODH reactors is done such that the energy required for generate $O_2$ for the ODH process would be minimized.

To enable combustion of $H_2$ at below auto ignition temperature of this compound (571° C.), a combustion catalyst (such as an iron-based catalyst) could be used in the retentate side of the CMDR reactor.

If a tube and shell heat exchanger type CMDR reactor is used, due to the endothermic nature of dehydrogenation reaction in this unit and no concern with hot spot formation, the desired dehydrogenation catalyst can optionally be loaded into the shell side. Loading the catalyst in the shell side can reduce the size of the reactor.

In addition to what is shown in FIG. 1 and FIG. 2, a portion of the air and/or hot reduced O2/air can be sent to the retentate side of the OMU, to enhance energy efficiency for heating up the OMU membrane to the desired activation temperature.

In addition to what is shown in FIG. 1 and FIG. 2, the effluent stream entering the CMDR reactor can be collected from a demethanizer or a C2-splitter bottoms of a steam cracker process and/or ODH process. Furthermore, it is possible that the mentioned units are shared between a ODH process and steam cracker process, in which case, the effluent from the shared units can be sent to the CMDR reactor. Somewhat similar integration is possible with oxidative coupling of methane, deep catalytic cracking, catalytic pyrolysis process, and propane dehydrogenation.

In some embodiments, a C2 Splitter 118 unit as shown in FIG. 1 will not be required when the use of the CMDR reactor is able to convert all or almost all unreacted ethane to ethylene, as shown in FIG. 2.

The integration of ODH process with CMDR process can also have the following benefits:
1) Increase one pass ethylene yield in the ODH process to convert all of the unreacted ethane to ethylene.
2) Reduce the overall operating expense and capital expense of the ODH process by the following means:
   a. provide a portion (or all) of the heat required to activate the $H_2$ membrane by ODH heat of reaction and/or combustion of the generated $H_2$.
   b. provide a portion of the heat required to activate the $O_2$ membrane unit by sending the hot-$O_2$-reduced air stream from the CMDR reactor directly to the $O_2$ membrane unit.
   c. optionally remove the C2-splitter unit from the ODH process due to using CMDR reactor to convert all the unreacted ethane to ethylene.
3) Generate $H_2$ as a new by-product of the ODH process which can then be sold/used in other petrochemicals/agricultural industries (such as for fuel cells, or other products such as methanol, urea, etc.).

EXAMPLES

Example #1: Catalyst Dehydrogenation

Dehydration catalysts were developed and tested with chemical formula of 1 wt. % Pt—(0-7.5) wt. % Zn—ETS-2. Note that ETS-2 stands for Engelhard titanosilicate-2. 3 grams of catalyst was loaded and pure ethane was fed into the reactor. The catalysts were tested with operating temperature of 509° C. and WHSV range of 0.80 $h^{-1}$ to 1.13 $h^{-1}$. Out of the tested catalysts, the 1 wt. % Pt—(2-7.5) wt. % Zn—ETS-2 at WHSV of 0.86 $h^{-1}$-1.13 $h^{-1}$ and reaction temperature of 509° C. and operating pressure of 1 atm showed the following activity/performance:

1 wt. % Pt—2 wt. % Zn—ETS-2 performance at WHSV of 1.13 h$^{-1}$, residence time=1.6 sec, GHSV=2214 h$^{-1}$, reaction reached equilibrium ethane conversion of ~5% with 100% selectivity towards ethylene, no coke formation (for max time=100 min), no catalyst deactivation at reaction conditions (for max time=100 min).

1 wt. % Pt—5 wt. % Zn—ETS-2 performance at WHSV of 0.89 h$^{-1}$, residence time=2.1 sec, GHSV=1744 h$^{-1}$, reaction reached equilibrium ethane conversion of ~5% with 100% selectivity towards ethylene, no coke formation (for max time=55 min), no catalyst deactivation at reaction conditions (for max time=55 min).

1 wt. % Pt—7.5 wt. % Zn—ETS-2 performance at WHSV of 0.86 h$^{-1}$, residence time=2.1 sec, GHSV=1685 h$^{-1}$, reaction reached equilibrium ethane conversion of ~5% with 100% selectivity towards ethylene, no coke formation (for max time=45 min), no catalyst deactivation at reaction condition (for max time=45 min).

Comparing the required residence time over the catalyst (1.6-2.1 sec) to minimum residence time required for the minimum CMDR reactor (0.2 sec), it can be inferred that combing the mentioned catalyst with the CMDR reactor would result in successful paraffin to olefin conversion.

Example #2: ODH Process Simulation

A process simulation was performed using AspenPlus® V8.6. The process flowsheet was divided into sections and each section was run using different equations of state (EoS). The EoS used for the ODH reactor section was SR-POLAR and STEAMNBS EoS and the Demethanizer-C2 splitter section was operated using SRK EoS.

The feed entering the ODH reactor is shown in Table 1. The feed enters the reactor at 300° C. and 465 kPag. The oxygen in the feed was maintained at 23.6 wt. % (18.4 mol %) in order for the feed to be outside the flammability envelope. Ethane conversion was assumed to be 74 mol %, giving the outlet (product) composition shown in Table 1.

TABLE 1

Feed to and Product from ODH Reactor

| Component | Feed (mass frac.) | Product (mass frac.) |
|---|---|---|
| CH$_4$ | 0.0030 | 0.0030 |
| C$_2$H$_4$ | 0.0004 | 0.2150 |
| C$_2$H$_6$ | 0.3624 | 0.0945 |
| C$_3$H$_8$ | 0.0022 | 0.0005 |
| CO | 0.0000 | 0.0218 |
| CO$_2$ | 0.0201 | 0.0552 |
| H$_2$O | 0.3474 | 0.5191 |
| H$_2$S | 0.0000 | 0.0000 |
| CH$_3$COOH | 0.0181 | 0.0803 |
| O$_2$ | 0.2357 | 0.0000 |
| ARGON | 0.0106 | 0.0106 |

The product from the ODH reactor goes through the separation units downstream of the ODH reactor to the inlet of the C2 splitter. The stream upstream of the C2 splitter is at −6.4° C. and 1855 kPag. The composition of this stream is as shown in Table 2. The stream at the bottom of the C2 splitter after the heat exchangers is at 19° C. and 550 kPag. The composition of this stream is shown in Table 2.

TABLE 2

Feed to and Bottoms Product from C2-Splitter

| Component | Feed (mass frac.) | Product (mass frac.) |
|---|---|---|
| CH$_4$ | 30 ppm | trace |
| C$_2$H$_4$ | 0.692 | 0.005 |
| C$_2$H$_6$ | 0.306 | 0.990 |
| C$_3$H$_8$ | 0.002 | 0.006 |

Example #3: CMDR Reactor Experiment

Published experimental work conducted by Eltron Research Inc. (Lowe et al, *Hydrogen Membrane Selection for a Water Gas Shift Reactor—Phase II*, Third Conference on Carbon Sequestration, Alexandria, VA, May 3-6, 2004) resulted in successful membrane development using group 4 elements and group 5 elements (Nb, Ta, V, Zr, etc.) and their alloys. This membrane was used for increasing the conversion of equilibrium-controlled water gas shift reaction by means of selectively removing H$_2$ from the product stream using the mentioned membrane at the operating temperature range of 340-440° C. and operating pressure up to 35 barg. The feed mixture was 37.3 mol % steam, 17.8 mol % CO$_2$, 41.4 mol % H$_2$, 3.3 mol % CO with balance of nitrogen.

The published project was to demonstrate that membrane disks, 16 mm diameter and 127 microns thick, could resist a differential pressure of at least 30 barg (3.0 MPag or 435 psig) while maintaining exceptionally high flux of hydrogen at essentially 100% hydrogen selectivity. Membranes were successfully tested for over 300 hours at 673 K (400° C.) at an absolute pressure on the feed side of 3.23 MPag (32.3 barg or 468 psig) and a differential pressure of 3.13 MPag (31.3 barg or 454 psig).

After eliminating rate limiting steps due to adsorption of impurities on both sides of the membrane and rate limiting steps due to gas phase diffusion, a hydrogen flux of 280 mL·minh$^{-1}$·cm$^{-2}$ (STP) was achieved for a 127 micron thick metal membrane at 440° C., using the target partial pressure of H$_2$ of 13.1 barg, an ideal H$_2$/He mixture in the gas feed, and a differential pressure of 31.0 barg. The flux was increased to 346 mL·minh$^{-1}$·cm$^{-2}$ (STP) using H$_2$ partial pressure in the feed of 29.0 barg in an ideal H$_2$/He mixture. For simulation work conducted in the proceeding examples, the lowest reported hydrogen flux was used because the H$_2$ partial pressure is closer to H$_2$ partial pressure for the lowest hydrogen flux (13.1 barg).

The H$_2$ recovery is not reported by Lowe et al (2004). For simulation work conducted in the following examples, the H$_2$ recovery was assumed to be 90%.

Example #4: ODH Integrated with CMDR Simulation

The stream to the feed to the C2 splitter, Feed 310 in FIG. 3, simulated as per Table 2, was fed to the inlet of this simulation. AspenPlus® software with Peng Robinson property method was used. To simulate a CMDR (as reported in Example #3), a simulation was created consisting of a Heater 302, an RStoic 304, and a Sep 306. Heat 308 is the heat input to heat the Feed 310 to the temperature required by RStoic 304. The reaction temperature in RStoic 304 was assumed to be 440° C. At this temperature, 0.4 mol % equilibrium ethane conversion and 1.4 mol % equilibrium propane conversion is expected. Assuming there is enough residence time inside the CMDR, all of the ethane and propane are converted to ethylene and propylene. The membrane was assumed to be compatible with $CH_4$, CO, $H_2$, paraffins and olefins. The $H_2$ recovery is not reported in Lowe et al (2004) so it was assumed to be 90%. Negligible pressure drop is assumed between the membrane side and the retentate side. The required energy for the heater block, Heat 308, can provided by exothermic ODH heat of reaction, exothermic heat of $H_2$ combustion produced in the CMDR, or other energy sources.

The results are presented in Table 3, and summarized below:

TABLE 3

| PROPERTY | DS-DRIER | RXN-FEED | RXN-PROD | PER-MEATE | RE-TENT-ATE |
|---|---|---|---|---|---|
| Temp. (° C.) | 15 | 440 | 440 | 440 | 440 |
| Pressure (bara) | 25.714 | 25.714 | 25.714 | 25.714 | 25.714 |
| Mass Vapor Fraction | 1 | 1 | 1 | 1 | 1 |
| Mass Flows (kg/hr) | 43915.42 | 43915.42 | 43915.42 | 703.98 | 43211.45 |
| Mass Fractions | | | | | |
| $CH_4$ | 0.015 | 0.015 | 0.015 | 0.000 | 0.015 |
| $C_2H_4$ | 0.626 | 0.626 | 0.873 | 0.000 | 0.887 |
| $C_2H_6$ | 0.265 | 0.265 | 0.000 | 0.000 | 0.000 |
| $C_3H_8$ | 0.001 | 0.001 | 0.000 | 0.000 | 0.000 |
| CO | 0.063 | 0.063 | 0.063 | 0.000 | 0.064 |
| $N_2$ | 0.030 | 0.030 | 0.030 | 0.000 | 0.030 |
| $H_2$ | 0.000 | 0.000 | 0.018 | 1.000 | 0.002 |
| $C_3H_6$ | 0.000 | 0.000 | 0.001 | 0.000 | 0.001 |
| Volume Flow (cum/hr) | 1186.10 | 3585.22 | 4498.74 | 810.05 | 3678.61 |

All of the unreacted ethane and unreacted propane present in the stream Feed 310 was converted to ethylene and propylene. The overall one pass ethylene yield can be increased from the yield of an ODH process to the yield integrating the ODH process and the CMDR.

The energy required to preheat stream Feed 310 going into the CMDR was found to be 11900 KW (Heat 308). Assuming hydrogen flux of 280 mL·minh$^{-1}$·cm$^{-2}$ (STP), the CMDR volume and residence time were 206 liters and 0.21 seconds. (Note the reported hydrogen flux is collected from example 3 for $H_2$ containing gas mixture with lowest tested $H_2$ partial pressure of 13.1 barg. This hydrogen flux enables us to estimate the CMDR volume and residence time.)

Example #5: Simulating Heat Integration by Burning Produced $H_2$

One means of activating the CMDR is to burn all of the $H_2$ generated in this reactor. The Peng Robinson property method was used. The feed stream Feed 412 in FIG. 4 was set to the same values as Feed 310 and was sent to RStoic 404. An air stream, Air Feed 420, was added to burn the $H_2$ in Permeate 414, and exits as Air Prod 426. The following assumptions were used for creating this simulation:

The effluent stream from H2Burn 406, NoH2 428, has 16 mol % $O_2$ via adjusting the flow rate of the air stream, Air Feed 420.

In RStoic 404, the exothermic $H_2$ combustion heat of reaction was first used to provide heat required for Heater 402, the balance remaining heat was used to preheat the effluent air stream, Air Prod 426.

The effluent air stream, Air Prod 426, temperature is 440° C. via adjusting the temperature of the feed air stream, Air Feed 420.

The results are shown in Table 4 and summarized below:

TABLE 4

| PROPERTY | AIR-FEED | AIR-PROD |
|---|---|---|
| Temp. (° C.) | 95.5 | 440.0 |
| Pressure (bara) | 25.714 | 25.714 |
| Mass Vapor Fraction | 1 | 1 |
| Mole Flows (kmol/hr) | 4084.45 | 4259.06 |
| $CH_4$ | 0.000 | 0.000 |
| $C_2H_4$ | 0.000 | 0.000 |
| $C_2H_6$ | 0.000 | 0.000 |
| $C_3H_8$ | 0.000 | 0.000 |
| CO | 0.000 | 0.000 |
| $N_2$ | 0.790 | 0.758 |
| $H_2$ | 0.000 | 0.000 |
| $C_3H_6$ | 0.000 | 0.000 |
| $O_2$ | 0.210 | 0.160 |
| $H_2O$ | 0.000 | 0.082 |
| Mass Flows (kg/hr) | 117838.1 | 118542.1 |
| Mass Fractions | | |
| $CH_4$ | 0.000 | 0.000 |
| $C_2H_4$ | 0.000 | 0.000 |
| $C_2H_6$ | 0.000 | 0.000 |
| $C_3H_8$ | 0.000 | 0.000 |
| CO | 0.000 | 0.000 |
| $N_2$ | 0.767 | 0.763 |
| $H_2$ | 0.000 | 0.000 |
| $C_3H_6$ | 0.000 | 0.000 |
| $O_2$ | 0.233 | 0.184 |
| $H_2O$ | 0.000 | 0.053 |
| Volume Flow (cum/hr) | 4869.7 | 9888.9 |

All of the heat required to activate the CMDR (11914.4 kW) is supplied by combusting $H_2$.

$H_2$ combustion generated excess heat beyond the CMDR activation heat requirement, which was used to preheat the effluent air stream Air Prod 426 from 95.5° C. to 440.0° C. This hot air stream could optionally be sent to the $O_2$ membrane unit to provide a portion of the activation heat for this unit, which typically requires approximately 850° C. to be activated.

Example #6: Simulating CMDR

The stream to the feed to the C2 splitter, Feed 310 in FIG. 3, was simulated as per Table 2, was fed to the inlet of this simulation. AspenPlus® software with Peng Robinson property method was used. To simulate a CMDR (as reported in Example #3), a simulation was created consisting of a Heater 302, an RStoic 304, and a Sep 306. Heat 308 is the heat input to heat the Feed 310 to the temperature required by RStoic 304. The reaction temperature in RStoic 304 was assumed to be 440° C.

The model had these restrictions:

The reaction temperature in RStoic 304 was 440° C. At this temperature, the ethane equilibrium conversion is 0.8 mol %, and the propane equilibrium conversion is 3 mol %. Assuming there is enough residence time inside the CMDR reactor, all the ethane and propane was respectively converted to ethylene and propylene. The membrane is compatible with $CH_4$, CO, $H_2$, paraffin and olefins.

$H_2$ recovery in the CMDR is 90%. This recovery is not reported in Example #3.

No pressure drop between membrane side and retentate side.

The required energy for Heater 302, can provided by the exothermic ODH heat of reaction, the exothermic heat of $H_2$ combustion (produced in the CMDR), or by other energy sources.

The simulation results are shown in Table 5 and summarized below:

TABLE 5

| PROPERTY | BTM-C2-S | RXN-FEED | RXN-PROD | PERMEATE | RETENTATE |
|---|---|---|---|---|---|
| Temp. (° C.) | 19.0 | 350.0 | 350.0 | 350.0 | 350.0 |
| Pressure (bara) | 5.5 | 5.5 | 5.5 | 5.5 | 5.5 |
| Mass Vapor Fraction | 1 | 1 | 1 | 1 | 1 |
| Mass Flows (kg/hr) | 11077.0 | 11077.0 | 11077.0 | 663.9 | 10413.1 |
| Mass Fractions | | | | | |
| $CH_4$ | 0.000 | 0.000 | 0.000 | 0.000 | 0.000 |
| $C_2H_4$ | 0.005 | 0.005 | 0.929 | 0.000 | 0.988 |
| $C_2H_6$ | 0.990 | 0.990 | 0.000 | 0.000 | 0.000 |
| $C_3H_8$ | 0.005 | 0.005 | 0.000 | 0.000 | 0.000 |
| CO | 0.000 | 0.000 | 0.000 | 0.000 | 0.000 |
| $N_2$ | 0.000 | 0.000 | 0.000 | 0.000 | 0.000 |
| $H_2$ | 0.0000 | 0.000 | 0.0667 | 1.000 | 0.007 |
| $C_3H_6$ | 0.000 | 0.000 | 0.005 | 0.000 | 0.005 |

All of the unreacted ethane and unreacted propane present in Feed 310 was converted to ethylene and propylene. This finding specifically implies that the overall one pass ethylene yield can be increased in the ODH process integrated with the CMDR.

The energy required to preheat RFeed 318 was found to be 3364.15 kW.

Assuming hydrogen flux of 280 mL·min$^{-1}$·cm$^{-2}$ (STP), the CMDR volume and residence time were respectively 193 liters and 0.18 seconds. (Note the reported hydrogen flux is collected from example 3 for $H_2$ containing gas mixture with lowest tested $H_2$ partial pressure of 13.1 barg. This hydrogen flux enables us to estimate the CMDR volume and residence time.)

Example #7: Comparison Between Energy Consumption Requirement to Generate $O_2$ by Cryogenic Air Separation and Hot Membrane $O_2$ Separation To understand the difference between energy requirements to generate $O_2$ by means of cryogenic air separation and hot membrane $O_2$ separation, the following literature data were used:

Linde in "Enhanced Cyrogenic Air Separation A proven Process applied to Oxyfuel Future Prospects", Dr.-Ing. Gerhard Beysel, 1st Oxyfuel Combustion Conference, Cottbus, Germany, Sep. 8, 2009, slide 20, reported the power required for a cryogenic air separation plant was 245 kWh/tonne $O_2$ (or 0.35 kW per m$^3$/hr of oxygen generated).

Fraunhofer IKTS in "Energy demand of oxygen membrane plants", Dr. Rer. Nat. Ralf Kriegel, Hermsdorf, Germany, reported a typical electricity demand of 0.2 kWh/m$^3$ STP $O_2$. If a portion of this energy gets generated by preheating the air inlet to this process, by using $H_2$ combustion, then the energy requirement can be decreased to even below 0.2 kWh/m$^3$ STP $O_2$ using this technology integrated with an ODH process.

From these references, 1 m$^3$/hr of $O_2$ can be produced with at least 43% less energy when hot membrane $O_2$ separation is used in place of cryogenic air separation unit in an ODH process. If heat integration occurs (i.e. by $H_2$ combustion to preheat the air feed), this energy difference may be become even more pronounced.

The detailed description, embodiments, and examples provided herein are intended for illustrative purposes only and not intended to limit the scope of the present disclosure, which should be understood to include various additional aspects, modifications or changes that would be apparent to those skilled in the art.

INDUSTRIAL APPLICABILITY

The present disclosure relates to a process for producing one or more C2-C4 alkanes. The process combines an oxidative dehydrogenation process with a catalyst membrane dehydrogenation reactor process to remove hydrogen.

The invention claimed is:

1. A process for the production of a C2-C4 alkene comprising:
   i) contacting in an oxidative dehydrogenation process a feed comprising a C2-C4 alkane and oxygen with a mixed metal oxide catalyst to produce a product stream comprising an unreacted C2-C4 alkane and a corresponding C2-C4 alkene; and
   ii) passing the product stream to a catalytic membrane dehydrogenation reactor process comprising a membrane containing a group 4 element or group 5 element to dehydrogenate at least a portion of the unreacted C2-C4 alkane to produce a permeate stream comprising hydrogen and a retentate stream comprising the corresponding C2-C4 alkene that is substantially free of hydrogen.

2. The process of claim 1, wherein the feed to the oxidative dehydrogenation process includes the C2-C4 alkane, oxygen, and a heat removal diluent gas comprised of carbon dioxide, steam, or nitrogen, or any combination thereof.

3. The process of claim 1, wherein the oxidative dehydrogenation process includes:
   i) contacting, in an oxidative dehydrogenation reactor, an oxygen containing gas and a C2-C4 alkane containing gas with an oxidative dehydrogenation catalyst to produce a product stream comprising the corresponding C2-C4 alkene and unreacted C2-C4 alkane, oxygen, carbon oxides, comprising carbon dioxide and carbon monoxide, oxygenates, comprising acetic acid, ethanol, acrylic acid, or maleic acid, or any combination thereof, and water;

ii) passing the product stream from i) through a process unit or several process units which remove oxygenates and water from said product stream;

iii) passing the product stream from ii) through a process unit or several process units which remove carbon dioxide from said product stream;

iv) passing the product stream from iii) through a dryer to remove water;

v) passing the product stream from iv) through a distillation tower to separate an overhead stream comprising C1 hydrocarbons from a bottoms stream comprising the C2-C4 alkane and the C2-C4 alkene; and vi) passing the bottom stream from v) to a catalytic membrane dehydrogenation reactor process.

4. The process of claim 3, wherein at step v) passing the product stream from iv) through a distillation tower to separate the overhead stream comprising C1 hydrocarbons comprises passing at least part of the overhead stream comprising C1 hydrocarbons to an oxygen membrane unit.

5. The process of claim 4, wherein the oxygen membrane unit comprises the permeate stream and the retentate stream, and at least part of the retentate stream of the oxygen membrane unit is recycled to the oxidative dehydrogenation process.

6. The process of claim 4, wherein producing a retentate stream comprising corresponding C2-C4 alkene that is substantially free of hydrogen comprises passing said stream to the oxygen membrane unit.

7. The process of claim 3, wherein at step v) passing the product stream from iv) through a distillation tower to separate an overhead stream comprising C1 hydrocarbons from the bottoms stream comprises passing the bottoms stream to a C2 Splitter.

8. The process of claim 1, wherein the catalytic membrane dehydrogenation reactor process comprises passing the retentate stream to a distillation column for separation of alkane from alkene.

9. The process of claim 3, wherein the process unit in step ii) comprises a quench tower.

10. The process of claim 3, wherein the several process units in step ii) comprise an air-cooled heat exchanger followed by a flash drum.

11. The process of claim 3, wherein a process unit is added upstream of the amine wash to remove residual oxygen.

12. The process of claim 3, wherein the process unit in step iii) comprises an amine wash unit.

13. The process of claim 12, wherein the amine wash unit is followed by a caustic tower.

14. The process of claim 1, wherein the catalytic membrane dehydrogenation reactor process is operated at a temperature range from about 350° C. to about 440° C.

15. The process of claim 1, wherein the catalytic membrane dehydrogenation reactor process is operated at a temperature range from about 340° C. to about 425° C.

16. The process of claim 1, wherein the catalytic membrane dehydrogenation reactor process is operated at a temperature range from about 325° C. to about 410° C.

17. The process of claim 1, wherein the membrane in the catalytic membrane dehydrogenation reactor process is operated at a pressure range between about 10 barg to about 25 barg.

18. The process of claim 1, wherein the membrane in the catalytic membrane dehydrogenation reactor process has at least about 85 mol % permeation selectivity for hydrogen.

19. The process of claim 1, wherein the membrane in the catalytic membrane dehydrogenation reactor process has at least about 90 mol % permeation selectivity for hydrogen.

20. The process of claim 1, wherein the membrane in the catalytic membrane dehydrogenation reactor process has at least about 95 mol % permeation selectivity for hydrogen.

21. The process of claim 1, wherein the membrane in the catalytic membrane dehydrogenation reactor process is an ionic membrane.

22. The process of any of claims 1 through 21, wherein the C2-C4 alkane comprises ethane.

23. The process of any of claims 1 through 21, wherein the C2-C4 alkene comprises ethylene.

24. The process of claim 1, wherein the group 4 element is selected from the group consisting of Ti, Zr and Hf.

25. The process of claim 1, wherein the group 5 element is selected from the group consisting of V, Nb and Ta.

26. The process of claim 1, wherein the membrane in the catalytic membrane dehydrogenation reactor process comprises Ti, Zr, Hf, V, Nb, or Zr, or any combination thereof.

27. The process of claim 1, wherein the membrane in the catalytic membrane dehydrogenation reactor process comprises Nb, Ta, V, or Zr, or any combination thereof.

* * * * *